United States Patent [19]

Castleman et al.

[11] Patent Number: 4,865,996
[45] Date of Patent: Sep. 12, 1989

[54] SORPTION/DESORPTION METHOD AND APPARATUS

[75] Inventors: Bruce W. Castleman, Kenneth City; Marion H. Cates; Eugene L. Szonntagh, both of Largo; Rex R. Walker, Clearwater; W. Frank Wilhite, Tampa, all of Fla.

[73] Assignee: Brunswick Corporation, Skokie, Ill.

[21] Appl. No.: 132,688

[22] Filed: Dec. 14, 1987

Related U.S. Application Data

[63] Continuation of Ser. No. 890,254, Jul. 28, 1986, abandoned, which is a continuation of Ser. No. 663,107, Oct. 22, 1984, abandoned.

[51] Int. Cl.$^4$ .................... B01D 53/06; B01D 53/08
[52] U.S. Cl. ................................. 436/161; 422/88; 422/89; 55/34; 55/60; 55/62; 55/181; 55/208
[58] Field of Search ............... 422/88, 89; 436/161; 55/208, 181, 33, 346, 60, 62, 59

[56] References Cited

U.S. PATENT DOCUMENTS

| | | | |
|---|---|---|---|
| 3,149,941 | 9/1964 | Barnitz et al. | 436/161 |
| 3,176,446 | 4/1965 | Siggelin | 55/62 |
| 4,249,904 | 2/1981 | Rounbehler et al. | 422/88 |
| 4,409,006 | 10/1983 | Mattia | 55/28 |
| 4,711,765 | 12/1987 | Cates et al. | 436/161 X |

Primary Examiner—Barry S. Richman
Assistant Examiner—Lynn M. Kummert
Attorney, Agent, or Firm—Wood, Dalton, Phillips, Mason & Rowe

[57] ABSTRACT

A gas analysis apparatus including a sorption bed and a receiver normally spaced apart from the sorption bed. A given flow path is defined between the sorption bed and the receiver for directing a gas to be analyzed across the sorption bed for adsorption thereby in an adsorption mode of operation of the apparatus. A drive relatively moves the sorption bed and the receiver closer together from their spaced apart condition to produce a volume reduction of the defined, given flow path across the sorption bed in a desorption mode of operation of the apparatus. A heater selectively heats the sorption bed to desorb the adsorbed gas from the bed into the volume reduced flow path. A gas analyzer is connected to the receiver for analyzing the desorbed gas.

14 Claims, 3 Drawing Sheets

SORPTION/DESORPTION METHOD AND APPARATUS

This application is a continuation of application Ser. No. 890,254, filed July 28, 1986, now abandoned which is a continuation of application Ser. No. 663,107 filed 10/22/84, now abandoned.

BACKGROUND OF THE INVENTION

1. Field of the Invention

The present invention relates to gas analyzers. Most specifically, the present invention is directed to a sorption/desorption apparatus for a gas analyzer.

2. Description of the Prior Art

Conventional sorption/desorption apparatus for gas analyzers have employed sorption/desorption beds having a constant flow volume during the sorption/desorption cycle. Such sorption/desorption beds do not provide for a significant enhancement of the sensitivity of the gas analysis system since such sensitivity is directly dependent on a constituent accumulation factor. Accordingly, to obtain a high sensitivity, it is critical to maximize the ratio of the sorption/desorption flow rates. The present invention provides a novel method and structure for maximizing such a ratio by utilizing a volume reduction during the desorption mode to affect the flow rate which equals the flow volume divided by the flow time. Thus, by maximizing the sorption/desorption flow volume ratio and minimizing the flow time ratio, the sensitivity or accumulation factor can be significantly increased to enhance the sensitivity of the analytical process.

SUMMARY OF THE INVENTION

An object of the present invention is to provide an improved sorption/desorption apparatus for a gas analyzer.

In accomplishing this and other objects, there has been provided, in accordance with the present invention a gas analysis apparatus comprising a sorption bed means having a first position for directing a gas to be analyzed in a gas flow path having a first gas flow volume across the sorption bed means in a sorption mode of operation to produce a sorption of a gas to be analyzed by the sorption bed means, means for receiving a desorbed sample comprising an enveloping cap which is parallel to and spaced apart from the sorption bed means, drive means for selectively transferring the sorption bed means from the first position to a second position in the interior of the enveloping cap in a desorption mode of operation to produce a second gas flow volume in the gas flow path across the sorption bed means which is less than the first gas flow volume, heating means for selectively heating the sorption bed means after the transfer of the sorption bed means into the means for receiving the desorbed sample by the drive means to desorb the sorbed gas from the sorption bed means into the second gas flow volume and gas analyzing means connected to the means for receiving the desorbed sample for analyzing the desorbed gas. A method for operating a gas flow apparatus including the steps of exposing a sorption bed means to a gas to be analyzed in a gas flow path having a first gas flow volume across the sorption means to produce a sorption of gas by the sorption means, transferring the sorption means to a means for receiving desorbed gas to produce a gas flow volume reduction in the gas flow path across the sorption means and heating the sorption means to desorb the sorbed gas from the sorption means into the reduced volume gas flow path.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

Detailed Description

Figure 1:
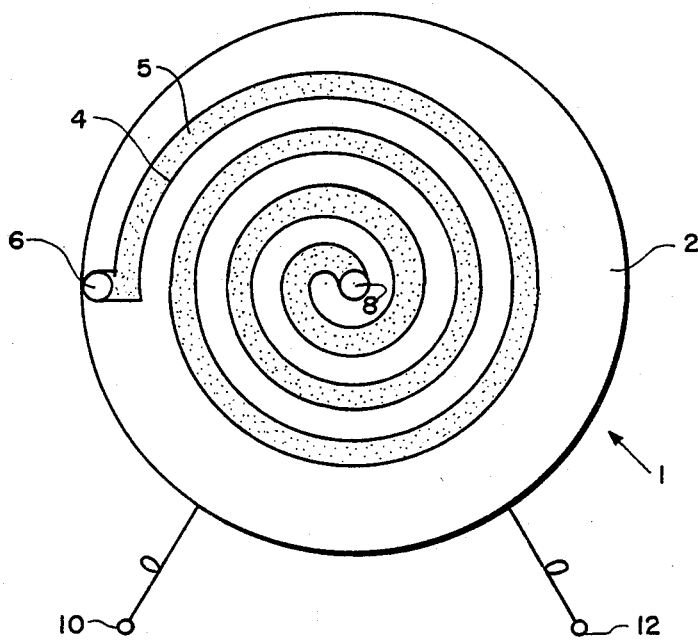
FIG. 1 is a top view of a sorption/desorption bed embodying an example of the present invention.

Referring to FIG. 1 in more detail, there is shown a sorption/desorption bed 1 having a support laminate 2 with a shallow circular spiral depression 4 defined on its outer surface. The spiral path 4 has its bottom surface coated with a suitable sorptive material 5 correlated to the gas constituents of interest. One end of the spiral path 4 is connected to an inlet 6 located at an outer periphery of the support laminate 2 while the other end of the spiral path 4 is connected to an outlet port 8 located at the center of the spiral path 4. It should be noted that while the sorption bed 1 is illustrated and described with a sorption material containing path 4 in the form of a regular circular spiral, the path 4 may be a non-circular spiral, a non-spiral labyrinth path, etc. The support surface 2 may be flat, curved, undulating, cylindrical, etc. and the inlet 6 and the outlet 8 may be at other locations than peripheral and axial. A pair of electrical connectors 10, 12 provide electrical connections to respective ends of a heater element embedded in the laminate 2, as hereinafter discussed.

Figure 2:
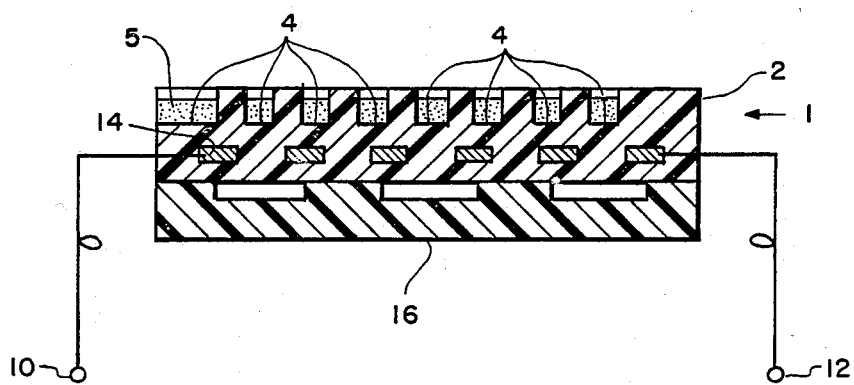
FIG. 2 is a cross-sectional illustration of the sorption/desorption bed shown in FIG. 1.

In FIG. 2, there is shown a cross-sectional illustration of the sorption bed 1. The laminate 2 which is made of a high temperature material such as a polyimide, which is preferably a high temperature, chemically inert polymer such as KAPTON manufactured by the DuPont Co., Wilmington, Delaware, has laminated or embedded therein a thin film labyrinth heater element such as the one known as 'Thermofoil' as manufactured by MINCO, Inc., Minneapolis, Minn. The pair of conductors 10 and 12 provide electrical connections to the ends of the heater element 14. The thickness of the heater laminate is preferably approximately 6.5 mil. To prepare the bed 1, the bottom surface of the spiral path 4 is initially coated with a thin layer of a polyimide adhesive diluted by dimethyl formamide. A fine powder of a sorptive material 5, e.g., Carbopack, a graphitized carbon black, is substantially uniformly sprinkled on the adhesive while the adhesive is still wet to form a thin coating, e.g., .1 mil, on the surface of the adhesive within the spiral path 4. The sorptive material is preferably a fine powder having a maximum particle size of 100 mesh. Subsequently, the coated bed 1 is heat-cured at approximately 220° C. for 30 minutes to thoroughly dry the adhesive and fix the sorptive material 5 thereto.

The final bed structure has the sorptive material in close thermal contact with the heater film. A sorption bed 1 having the aforesaid structure and having a surface area of approximately 1 square inch require only approximately 1.2 watts of power to energize the heater element 14. Accordingly, the heater element 14 may be energized for flash heating of the sorptive material to produce a desorption of the sample retained therein by a capacitive discharge through the heater element to produce a heating cycle of approximately 0.1 seconds. A rigid support backing 16 is used to provide a support surface for the laminate 2 to enable the sorption bed 1 to be physically displaced in the gas analysis apparatus, as described hereinafter.

Figure 3:
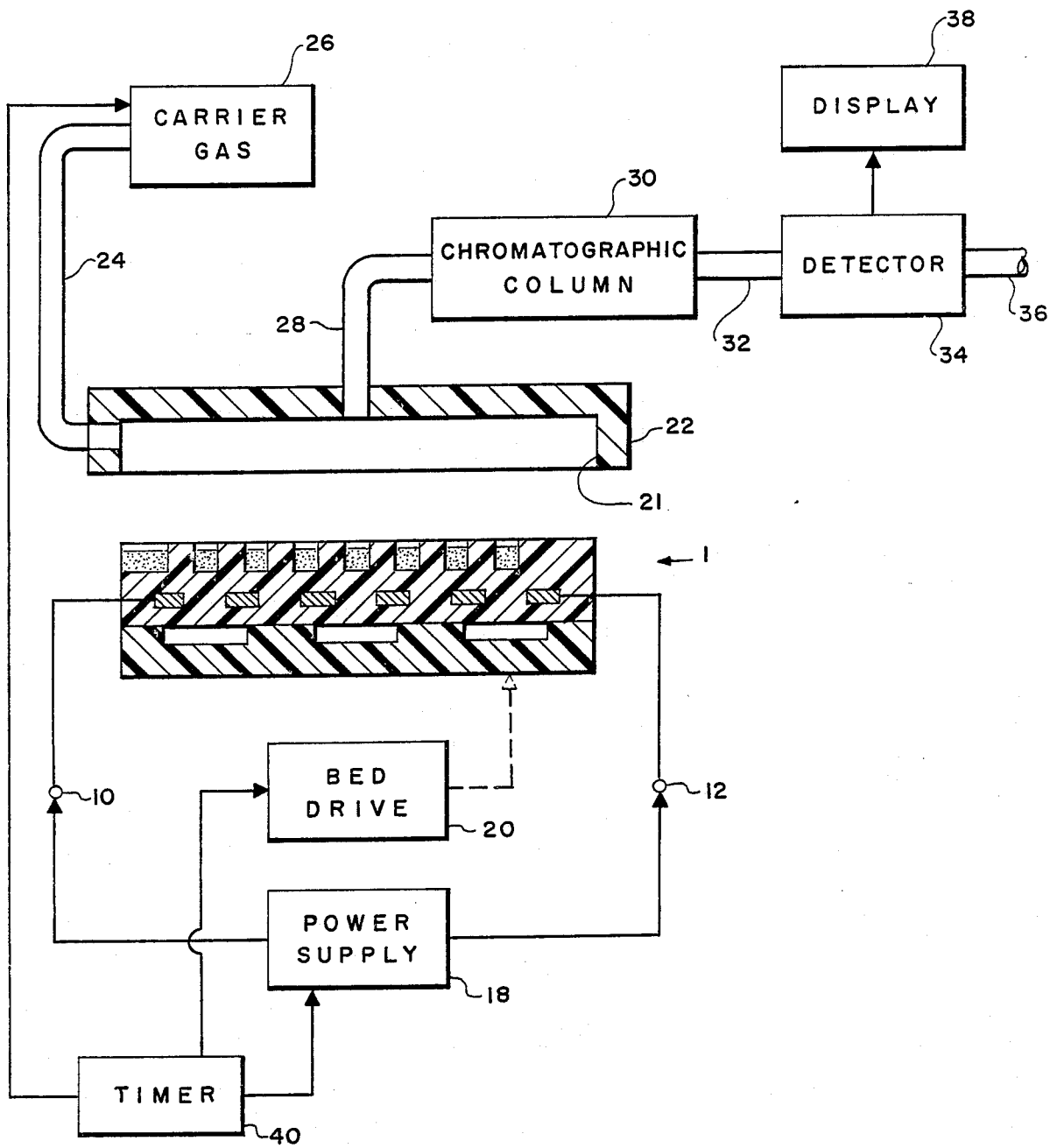
FIG. 3 is a gas analyzing apparatus utilizing the sorption/desorption bed shown in FIGS. 1 and 2 in a sorption mode and FIG. 4 is a gas analyzing apparatus utilizing the sorption/desorption bed shown in FIGS. 1 and 2 in a desorption mode.

In FIG. 3, there is shown a preferred embodiment of a gas analysis apparatus utilizing the sorption bed 1 shown in FIGS. 1 and 2. The sorption bed 1 is located on a bed drive 20 which is used to propel the sorption bed 1 toward a cover or cap 22 having a recess 21 into which the sorption bed 1 is arranged to fit with the outer surfaces of the bed 1 contacting the surface of the recess 21 to restrain a gas flow along the path 4. One end of an inlet pipe 24 extending through an outer periphery of the cover 22 is connected to a source of a carrier gas 26. The carrier gas source 26 is a selectively operable carrier gas source which may be energized to provide a carrier gas flow into the pipeline 24. One end of a second pipeline 28 extends through the center of the cover 22 and is arranged to communicate with the center outlet 8 of the sorption bed 1 when the bed 1 is within the cap 22. The other end of the pipeline 28 is connected to the inlet of a chromatographic column 30. An outlet 32 from the column 30 is connected to a constituent detector 34 having a gas vent 36. An output signal from the detector 34 is connected to a display 38 to produce a display representative of the detected constituent in the gas sample being analyzed. A selectively operable power supply 18 is connected to the heater terminals 10 and 12 to produce a selective energization of the heater element. A control timer 40 is connected to the carrier gas source 26, the power supply 18 and the bed drive 20 to synchronize the operation thereof.

In the position in FIG. 3, the sorption bed 1 is in a sorption mode wherein a gas to be analyzed is allowed to flow across the surface of the sorption bed 1 to be adsorbed by the sorption material located within the spiral on the sorption bed 1. Thus, the sorption bed 1 may be located within an enclosure (not shown) through which the gas to be analyzed is permitted to flow. The cap 22 could be part of a wall of such an enclosure to assist in guiding the sample gas across the spiral path of the sorption bed 1. The bed 1 would, of course, be spaced from the cap 22 and attached to the bed drive 20. At the end of the sorption cycle, the bed drive 20 is energized by the timer 40 to drive the sorption bed 2 into the cap 22. Modifications to the aforesaid apparatus such as having the bed 1 and the cap 22 as the moving component, having the bed 1 and the cap 22 both moving components, etc. may occur to those skilled in the art without departing from the scope of the present invention.

Figure 4:
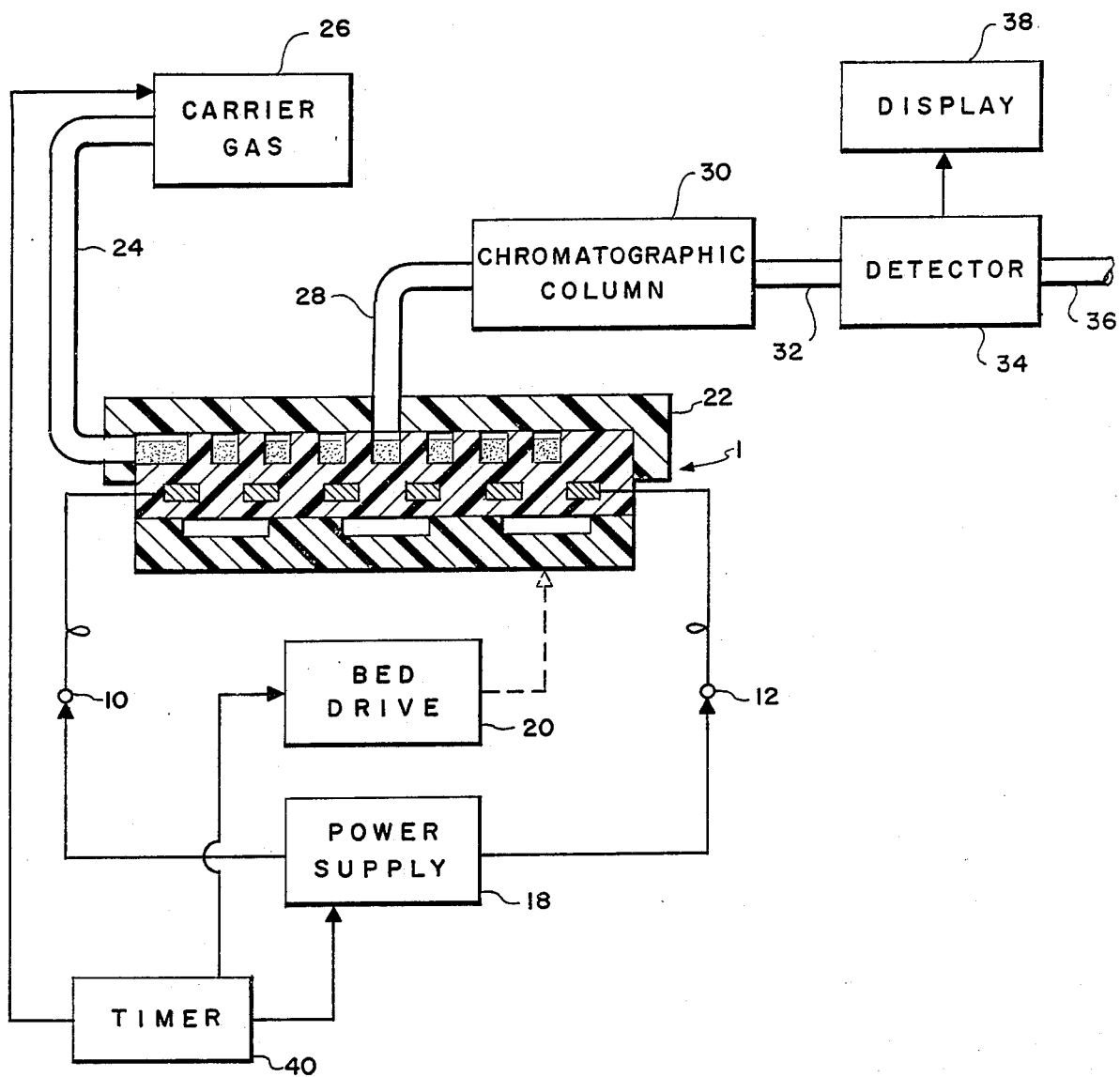

In FIG. 4, there is shown an illustration of the gas analyzing apparatus shown in FIG. 3 with the sorption bed 1 in a desorption mode. In this mode, the sorption bed 1 is driven by the bed drive 20 into the cap 22 and retained therein during the desorption cycle. After the sorption bed 1 is located within the cap 22, the timer 40 is arranged to energize the carrier gas source 26 and the power supply 18. The energization of the power supply 18 is effected to produce a flash heating of the sorption bed 1 to desorb the adsorbed sample from the sorption bed 1. Concurrently, the carrier gas source 26 produces a flow of a carrier gas through the space above the spiral path 4 through the volume defined between the surface of the material 5 and the adjacent surface of the recess 21 to drive the eluted sample from the sorptive material ino the pipe 28 and the chromatographic column 30. Ultimately, the sample is transported through the column 30 and the pipe 32 into the detector 34. The detector 34 is arranged to detect the constituent or constituents of interest before the sample is vented from the vent 36. An output signal from the detector 34 representative of the detected constituent or constituents is displayed on the display 38. Since the volume reduction provided by driving the sorption bed 1 into the cap 22 is effective to provide accumulation or concentration factors in excess of 10,000, it enables the gas analyzing apparatus to achieve very fast desorption time, e.g., 0.1 seconds, and an overall analysis time of less than 1 minute including the sample travel time through the chromatographic column 30. By a proper selection of the dimensions of the cap 22 and the space above the sorptive material 5, the volume for desorption can be minimized, e.g., 100 microliters. This volume coupled with the large volume of sample air during the sorption mode enables the attainment of the aforesaid accumulation factor of over 10,000. The path 4 of the sorption bed 1 serves as a flow channeling device to prevent voids in the eluted sample, and the elimination of the broadening of the desorption peak whereby the desorbed matter is eluted into the gas chromatographic column 30 as a narrow sample slug similar to the slug-type sample introducing valves of conventional gas chromatographs.

Accordingly, it may seen that there has been provided, in accordance with the present invention, an improved sorption/desorption gas analysis apparatus.

The embodiments of the present invention in which an exclusive property or privilege is claimed are defined as follows:

1. A gas analysis apparatus comprising
    a sorption bed means having a first position for directing a gas to be analyzed in a gas flow path having a first gas flow volume across said bed means in a sorption mode of operation to produce a sorption of a gas to be analyzed by said sorption bed means,
    means for receiving a desorbed sample from said sorption bed means, said first position being defined by said means for receiving being spaced apart from said sorption bed means,
    drive means for selectively transferring said sorption bed means from said first position to a second position defined by said sorption bed means being placed together with said means for receiving in a desorption mode of operation to produce a volume reduction in said gas flow path across said sorption bed means with a second gas flow volume which is less than said first gas flow volume,
    heating means for selectively heating said sorption bed means after said transfer of said sorption bed means to said means for receiving by said drive means to desorb said sorbed gas from said sorption bed means into said second gas flow volume and
    gas analyzing means connected to said means for receiving for analyzing the desorbed gas.

2. A gas analysis apparatus as set forth in claim 1 wherein said means for receiving includes a selectively operable carrier gas source means for providing a carrier gas to propel desorbed gas from said sorption bed means through said reduced gas flow path.

3. A gas analysis apparatus as set forth in claim 2 wherein said heating means includes timer control means for synchronizing the operation of said drive means, said carrier gas source means and said heater means.

4. A gas analysis apparatus as set forth in claim 3 wherein said carrier gas source means is operated to provide said carrier gas concurrently with the heating of said sorption bed means by said heater means.

5. A gas analysis apparatus as set forth in claim 1 wherein said gas analyzing means includes a gas chromatographic means for analyzing gas desorbed from said sorption bed means.

6. A gas analysis apparatus as set forth in claim 5 wherein said means for receiving further includes a selectively operable carrier gas means providing a carrier gas to propel desorbed gas from said sorption bed means through said reduced gas flow path to said gas chromatographic means.

7. A gas analysis apparatus as set forth in claim 6 wherein said heating means includes timer control means for synchronizing the operation of said drive means, said carrier gas source means and said heater means to operate said gas source means to provide said carrier gas concurrently with the heating of said sorption bed means by said heater means.

8. A gas analysis apparatus as set forth in claim 1 wherein said sorption bed means includes a support means having an outside surface, a labyrinth gas flow path defining means on said outside surface of said support means and a sorptive material fixed in a path defined by said labyrinth gas flow path defining means.

9. For use in a gas analysis apparatus, a gas flow apparatus comprising:
sorption bed means;
receiving means normally in a position spaced apart from the sorption bed means and defining a given flow path therebetween for directing a gas to be analyzed across the sorption bed means for adsorption thereby in an adsorption mode of operation of the apparatus; and
means for relatively moving the sorption bed means and the receiving means closer together from the spaced apart position to produce a volume reduction of said defined, given flow path therebetween across the sorption bed means in a desorption mode of operation of the apparatus.

10. The gas flow apparatus as set forth in claim 9, including heating means for selectively heating said sorption bed means to desorb adsorbed gas from the bed means into the volume reduced flow path.

11. The gas flow apparatus as set forth in claim 9, including gas analyzing means connected to said receiving means for analyzing desorbed gas.

12. A method of operating a gas flow apparatus for use in a gas analysis apparatus, comprising the steps of:
providing sorption bed means;
providing receiving means in a normally spaced apart position from the sorption bed means and defining a given flow path therebetween for directing a gas to be analyzed across the sorption bed means for adsorption thereby in an adsorption mode of operation of the apparatus; and
relatively moving the sorption bed means and the receiving means closer together from the spaced apart position to produce a volume reduction of said defined, given flow path therebetween across the sorption bed means in a desorption mode of operation of the apparatus.

13. The method of claim 12, including the step of selectively heating said sorption bed means to desorb adsorbed gas from the bed means into the volume reduced flow path.

14. The method of claim 12, including the step of analyzing desorbed gas by analyzing means connected to the receiving means.

* * * * *